United States Patent [19]

Yaron et al.

[11] 4,314,936

[45] Feb. 9, 1982

[54] SUBSTRATES FOR THE QUANTITATIVE ASSAY OF ENZYMES AND SUCH ASSAY

[75] Inventors: Arieh Yaron; Amos Carmel, both of Rehovot, Israel

[73] Assignee: Yeda Research and Development Co., Ltd., Rehovot, Israel

[21] Appl. No.: 211,794

[22] Filed: Dec. 1, 1980

Related U.S. Application Data

[63] Continuation-in-part of Ser. No. 48,260, Jun. 13, 1979, abandoned.

[30] Foreign Application Priority Data

Jun. 16, 1978 [IL] Israel ........................................ 54940
Aug. 21, 1980 [IL] Israel ........................................ 60888

[51] Int. Cl.$^3$ ...................... C07C 103/52; C12Q 1/36
[52] U.S. Cl. .................................. 260/112.5 R; 435/24
[58] Field of Search .................... 260/112.5 R; 435/24

[56] References Cited

U.S. PATENT DOCUMENTS 3,884,896 5/1975 Blomback et al. ........... 260/112.5 R
3,886,136 5/1975 Claeson et al. .............. 260/112.5 R

OTHER PUBLICATIONS

Chem. Abstr. 86, (1977) 39312d.
Chem. Abstr. 72, (1970) 51996y.

*Primary Examiner*—Delbert R. Phillips
*Attorney, Agent, or Firm*—Browdy and Neimark

[57] ABSTRACT

According to the present invention there are provided novel substrates for the determination of enzymes, and especially of the peptide hydrolases such as angiotensin-converting enzyme, trypsin and similar enzymes, and aminopeptidase-P, and to a process for the determination of these enzymes, which comprises contacting a biological fluid containing said enzyme with said substrate, which is cleaved, resulting in a pronounced fluorescence which is measured, thus giving a quantitative measure of the enzyme.

19 Claims, No Drawings

SUBSTRATES FOR THE QUANTITATIVE ASSAY OF ENZYMES AND SUCH ASSAY

RELATION TO OTHER APPLICATIONS

The present application is a C.I.P. patent application of U.S. patent application Ser. NO. 048,260 filed on June 13, 1979, now abandoned.

BACKGROUND OF THE INVENTION

The preparation of a highly specific substrate for a given proteolytic enzyme usually requires the synthesis of specific oligopeptide of sufficient length to interact with as many subsites of the particular active site as possible. The hydrolysis of such an oligopeptide can be followed by a number of methods such as colorimetry, potentiometry, or spectroscopy. The latter method is usually preferred because of high sensitivity and convenience.

Spectroscopic monitoring of proteolytic activity is possible only if a spectral change occurs during the cleavage of a specific bond linking a suitable chromophore to the rest of the molecule.

DESCRIPTION OF THE PRIOR ART

A variety of chromophore-bearing oligopeptide derivatives have been successfully developed and utilized in assaying proteolytic enzymes. The most sensitive spectroscopic assay makes use of fluorescent groups as chromophores. Among such substrates it is worth mentioning the naphthalene and coumarine derivatives of amino acids or peptides which have been employed in the assays of a variety of proteolytic enzymes. The intact substrates are only poorly fluorescent, whereas the free fluorophores, which are liberated by enzymic hydrolysis, are highly fluorescent.

In the above spectrophotometric methods the fluorophore has to be linked directly to the bond undergoing enzymic cleavage. Most of the fluorophores used are bulky aromatic groups, different in nature from the amino acid residues that usually occur in natural substrates. The necessity of placing such bulky groups directly at the point of catalytic cleavage, as in the case in the above mentioned fluorogenic substrates, often represents a marked drawback. Also, the cleavable bond of the synthetic derivative differs from the joining the amino acid residues of the corresponding native substrates.

A relatively recent development in construction of fluorogenic substrates follows an approach that allows the preparation of derivatives with an uninterrupted peptide chain. A fluorescent group is attached to one part of the molecule and another group, that can quench the fluorescence, is linked to another part. The interaction between the two groups is quite efficient even when they are separated by several amino acid residues. Cleavage of the peptide chain at any point between the interacting groups results in separation between them, causing the appearance of fluorescence which is an accurate and sensitive measure of the number of substrate molecules cleaved.

OBJECT OF THE INVENTION

According to the present invention there are provided substrates designed to be cleaved by enzymatic action, said cleavage being accompanied by a raise of fluorescence, the measurement of which is indicative of the quantity of the enzyme present. More particularly the invention relates to substrates for the quantitative and specific determination of classified and hitherto unclassified enzymes of the type: peptide dipeptide hydrolase E.C. 3.4.15-, especially the human serum angiotensin I-converting enzyme; of the type aminoacyl peptidohydrolase E.C. 3.4.11-, especially the hitherto unclassified aminoacylproline aminopeptidase present in human serum, the bacterial aminopeptidase P and leucine aminopeptidase; and of the type peptide peptidohydrolase E.C. 3.4.4.-, especially such that break down peptides or proteins at the carboxylic side of arginine or lysine, e.g. trypsin, thrombin, plasmin, kallikrein, urokinase, Factor Xa. The substrates may further be used for the study of reactions in which such enzymes are formed, inhibited or consumed, and also for the determination of factors which affect or participate in such reactions, for example the determination of proenzyme activators, antienzymes and enzyme inhibitors.

SUMMARY OF THE INVENTION

According to the invention there are provided substrates for the quantitative determination of proteolytic enzymes such as aminopeptidases, dipeptidyl carboxypeptidases, and trypsin-like peptidyl peptide hydrolases. There is provided a quantitative assay for the determination of enzymes adapted to cleave certain substrates resulting in fluorescence, and especially for the determination of angiotensin I-converting enzyme, aminopeptidase P, and trypsin-like enzymes in biological fluids such as serum and the like.

The novel quantitative assay is based on the use of intramolecularly quenched fluorogenic substrates composed of an uninterrupted peptide chain, in which a fluorescent group is attached to one part of the molecule and another group that can quench the flourescence of the first group by intramolecular collision is linked to another part. The interaction between the two groups is quite effecient even when they are separated by several amino acid residues. Cleavage of the peptide chain at any point between the interacting groups results in separation between the two groups, causing the appearance of fluorescence which is an accurate and sensitive measure of the number of substrate molecules cleaved. When the amino acid sequence is designed according to specificity requirements of a particular enzyme, the first cleavage which is the only one monitored by this method, occurs preferentially by the enzyme of interest.

Some peptide substrates with hydrolysable peptide bonds in which a fluorescent group and a quenching group interact intramolecularly and in which cleavange of the hydrolysable link produces the appearance of fluorescence have been reported in literature for the enzyme carboxypeptidase and trypsin. In such substrates fluorophore and quencher interact through non-radiative electronic excitation energy transfer between the fluorescent donor and a suitable acceptor. This transfer is not mediated by direct contact of the two groups, and depends on the spectral overlap between the emission spectrum of the donor and the absorption spectrum of the acceptor. Therefore, the fluorophore-quencher pair has to be chosen in accordance with these requirement and are not subject of the present invention. In the fluorophore-quencher pairs which are dealt with here, quenching occurs between a quencher having an absorption band which does not overlap with the emission spectrum of the fluorophore. This makes possible the use of smaller groups, the choice of which is not restricted by the condition of spectral overlap. Proper incorporation of the fluorophore and quencher renders the peptide chain in its natural sequence, making possible the design of highly specific substrates.

The novel substrates which have a high susceptibility to peptidyl dipeptide hydrolases (E.C. 3.4.15) are represented by the general formulas (1) or (2):

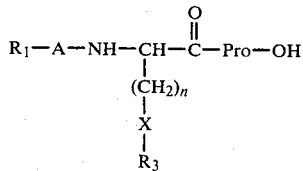
(1)

or salts thereof, where $R_1$ is selected from the group consisting of 1-dimethylaminonaphtalene-5-sulfonyl, 2-aminobenzoyl, 1.8-aminonaphtalene-sulfonyl, anthracene-9-carbonyl, fluoresceinyl, tetrabromofluoresceinyl ("eosinyl"), and rhodaminyl; A is selected from the group consisting of glycyl, L-alanyl, L-leucyl, L-phenylalanyl, and L-isoleucyl; n is 1-6; X is selected from the group consisting of a single bond, a carbonyl and imine (NH) group; $R_3$ is selected from the group consisting of nitrophenyl, dinitrophenyl, trinitrophenyl, nitrobenzyloxycarbonyl, dinitrobenzyloxycarbonyl, trinitrobenzyloxycarbonyl, nitrobenzoyl, dinitrobenzoyl, trinitrobenzoyl, ω-nitrophenylalkylamine having 1-4 carbon atoms in a straight chain and ω-trinitrophenylalkylamine having 1-4 carbon atoms in a straight chain; and

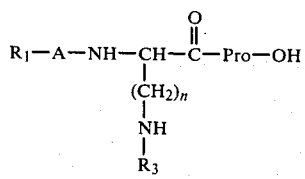
(2)

or salts thereof, where $R_1$ is selected from mono-, di- or trinitrophenyl alkyloxycarbonyl with 7-12 carbon atoms, a mono-, di-, or trinitrophenyl alkyl carbonyl with 7-12 carbon atoms; A is selected from internal amino acid residues, glycyl, L-alanyl, L-leucyl, L-phenylalanyl, L-isoleucyl, n is 3 or 4; $R_3$ is selected from the group consisting of 1-dimethylaminonaphtalene-5-sulfonyl, 2-aminobenzoyl, 1.8-aminonaphtalene-sulfonyl, anthracene-9-carbonyl, umbeliferone, fluoresceinyl, tetrabromofluoresceinyl ("eosinyl") and rhodaminyl.

Substrates with a high susceptibility to α-aminoacyl-peptide hydrolases (E.C. 3.4.11) which are represented by the formula

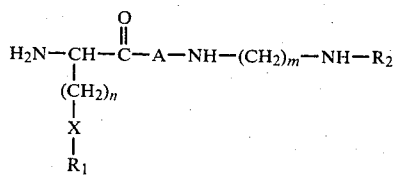
(3)

or the salts thereof, wherein n is selected from 1, 2, 3 and 4; X is selected from a single bond, secondary amino group, carbonyl; $R_1$ is selected from nitrophenyl, dinitrophenyl, trinitrophenyl, nitrobenzyloxycarbonyl, dinitrobenzyloxycarbonyl, trinitrobenzyloxycarbonyl, nitrobenzoyl, dinitrobenzoyl, trinitrobenzoyl, ω-nitrophenylalkylamine having 1-4 carbon atoms in a straight chain, ω-dinitrophenylalkylamine having 1-4 carbon atoms in a straight chain, and ω-trinitrophenylalkylamine having 1-4 carbon atoms in a straight chain; A is selected from the group consisting of one or two internal amino acid residues L-prolyl, glycyl, L-alanyl, L-leucyl, L-phenylalanyl, L-tyrosyl, L-lysyl, L-glutamyl, L-prolyl-L-prolyl and glutaminyl; m is selected from 1-6; $R_2$ is selected from the group consisting of 1-dimethylaminonaphtalene-5-sulfonyl, 2-aminobenzoyl, 1.8-dimethylaminonaphtalene-sulfonyl, anthracene-9-carbonyl, umbeliferone, fluoresceinyl, tetrabromofluoresceinyl ("eosinyl") and rhodaminyl.

Substrates with a high susceptibility to α-aminoacyl-peptide hydrolases (E.C. 3.4.11) which are represented by the formula:

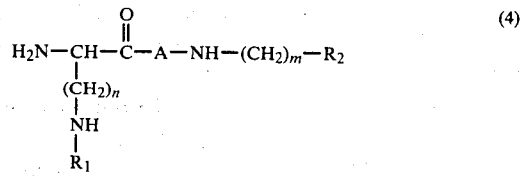
(4)

or the salts thereof, where n is 3 or 4; $R_1$ is selected from 1-dimethylaminonaphtalene-5-sulfonyl, 2-aminobenzoyl, 1.8-aminonaphtalene-sulfonyl, anthracene-9-carbonyl, umbeliferone, fluoresceinyl, tetrabromofluoresceinyl ("eosinyl"), rhodaminyl; A is selected from L-alanyl, L-alanyl-L-alanyl, L-phenylalanyl, L-phenylalanyl-L-alanyl, L-alanyl-L-phenylalanyl, L-alanyl-L-leucyl, L-leucyl-L-alanyl, L-leucinyl, L-isoleucinyl, L-isoleucinyl-L-alanyl and L-alanyl-L-isoleucinyl; m is an integer of 1 to 6; $R_2$ is selected from nitrophenyl, dinitrophenyl, trinitrophenyl, $Cbz(NO_2)$-NH, $Cbz(NO_2)_2$-NH, $Cbz(NO_2)_3$-NH, where Cbz designates benzyloxycarbonyl, $R_3$-Phe($NO_2$)-NH, $R_3$-Lys (Dnp)-NH, $R_3$Lys(Tnp), where $R_3$ is hydrogen or an acyl radical with 1-6 carbon atoms in a straight chain.

Substrates with a high susceptibility to trypsin (E.C. 3.4.21:4) and other proteolytic enzymes of the type 3.4.21, especially such that break down peptides or proteins in the peptide chain at the carboxylic side of arginine or lysine, which substrates are represented by the general formulas (5) or (6):

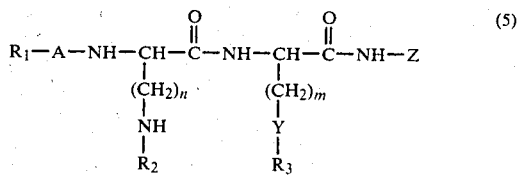
(5)

or the salts thereof; where $R_1$ is selected from the group consisting of 1-dimethylaminonaphtalene-5-sulfonyl, 2-aminobenzoyl, 1.8-aminoaphtalene-sulfonyl, anthracene-9-carbonyl, umbeliferone, fluoresceinyl, tetrabromofluoresceinyl ("eosinyl"), rhodaminyl; A may be selected from glycyl, L-valyl, L-leucyl, L-prolyl and L-phenylalanyl-L-valyl; n is 3 or 4; $R_2$ is selected from hydrogen and guanyl; m is an integer of 1 to 4, Y is selected from a single bond, carbonyl and an imine (NH) group; $R_3$ is selected from nitrophenyl, dinitrophenyl, trinitrophenyl, nitrobenzyloxycarbonyl, dinitrobenzyloxycarbonyl, trinitrobenzyloxycarbonyl, ω-nitrophenylalkyl having 1-4 carbon atoms in a straight chain, ω-trinitrophenylalkylcarbonyl having 1-4 carbon atoms in a straight chain, ω-nitrophenylalkylamino having 1-4 carbon atoms in a straight chain, ω-dinitrophenylalkylamino having 1-4 carbon atoms in a straight chain and ω-trinitrophenylalkylamino having 1-4 carbon atoms in a straight chain; Z is selected from hydrogen, an acyl having from 1 to 6 carbon atoms, a C-terminal amino acid residue glycyl, L-alanyl, L-leucyl, L-phenylalanyl, L-prolyl, L-glutaminyl and their respective amides.

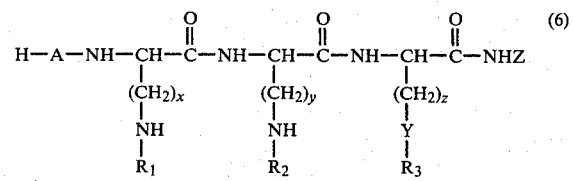

(6)

or salts thereof; where A is selected from glycyl, D-valyl, L-valyl, D-phenylalanyl and L-phenylalanyl; x is 2, 3, or 4; $R_1$ is selected from the group consisting of 1-dimethylaminonaphtalene-5-sulfonyl, 2-aminobenzoyl, 1.8-aminonaphtalene-sulfonyl, anthracene-9-carbonyl, fluoresceinyl, tetrabromofluoresceinyl ("eosinyl"), rhodaminyl; y is 3 or 4; $R_2$ is hydrogen or guanyl; z is an integer of 1 to 4; Y is selected from a single bond, carbonyl and imine (NH); $R_3$ is selected from the group consisting of nitrophenyl, dinitrophenyl, trinitrophenyl, nitrobenzyloxycarbonyl, dinitrobenzyloxycarbonyl, trinitrobenzyloxycarbonyl, ω-nitrophenylalkyl having 1-4 carbon atoms in a straight chain, ω-trinitrophenylalkylcarbonyl having 1-4 carbon atoms in a straight chain, ω-nitrophenylalkylamino having 1-4 carbon atoms in a straight chain, ω-dinitrophenylalkylamino having 1-4 carbon atoms in a straight chain and ω-trinitrophenylalkylamino having 1-4 carbon atoms in a straight chain.

Substrates of this type can be prepared which are "tailored" for the determination of various enzymes, which cleave such substrates resulting in fluorescence which is measured and which is indicative of the quantity of the enzyme measured.

According to the present invention substrates are provided for the determination of various enzymes.

The invention is illustrated, amongst others, with reference to the quantitative determination of angiotensin I-converting enzyme, and for this specific purpose there has been synthesized the substrate of general formula (1), wherein $R_1$ is 2-aminobenzoyl, A is glycyl, X is a single bond, n is 1, $R_3$ is 4-nitrophenyl namely ABz-Gly-Phe(NO$_2$)-Pro-OH wherein ABz designates 2-aminobenzoyl in which the fluorescence of the ABz group is quenched by intramolecular collision with the Phe(NO$_2$) residue. Hydrolytic cleavage of the Gly-Phe(NO$_2$) peptide bond by the enzyme cancels the interaction between the two groups and results in appearance of fluorescence. The efficient intramolecular quenching in the intact substrate, the high quantum yield and spectral characteristics of the ABz group endows the assay with high sensitivity. The amino acid sequence of the peptide has been chosen to ensure high specificity toward angiotensin I-converting enzyme. Unlike other known methods, the new assay requires no extraction, dialysis or other manipulations. The test is rapid and requires less than 100 μl of human serum.

Another example is illustrated with reference to the quantitative determination of aminoacyl proline aminopeptidase (E.C. 3.4.11.9 and the like) and for this specific purpose there has been synthesized the substrate of the general formula (3) wherein n is 1, X is a single bond, $R_1$ is 4-nitrophenyl, A is L-proline, m is 2 and $R_2$ is 2-aminobenzoyl, namely Phe(NO$_2$)-Pro-Eda-ABz where Eda is NH—CH$_2$—CH$_2$—NH and ABz is 2-aminobenzoyl and the substrate of the general formula (3) wherein n is 1, X is a single bond, $R_1$ is 4-nitrophenyl, A is L-prolyl-L-prolyl, m is 2 and $R_2$ is 2-aminobenzoyl, namely Phe(NO$_2$)-Pro-Pro-Eda-ABz which have been synthesized and found to be adequate for the quantitative determination of aminopeptidase P. This enzyme is known to cleave a peptide bond formed between an amino-terminal amino acid residue and a prolyl residue in low and high molecular weight peptides.

Cleavage of the Phe(NO$_2$)-Pro bond by the enzyme cancels the interaction between the fluorescent ABz group and the quenching Phe(NO$_2$) and results in appearance of fluorescence. The fluorimetric assay makes possible the simple, highly sensitive determination of small quantities of bacterial aminopeptidase P, and of its mammalian analogues including the calf-lung and the human-serum aminoacyl proline aminopeptidase.

The invention is illustrated also with reference to the quantitative determination of trypsin and for this specific purpose there has been synthesized the substrate of the general formula (5) wherein $R_1$ is 2-amino benzoyl, A is glycyl, n is 1, $R_2$ is guanyl, m is 1, Y is a single bond, $R_3$ is 4-nitrophenyl and z is hydrogen, namely ABz-Gly-Arg-Phe(NO$_2$)-NH$_2$ in which the fluorescence of the ABz group is quenched by intramolecular collision with the Phe(NO$_2$) residue. Hydrolytic cleavage of the Arg-Phe(NO$_2$) peptide bond by the enzyme cancels the interaction between the two groups and results in appearance of fluorescence. The efficient intramolecular quenching in the intact substrate, the high quantum yield and spectral characteristics of the ABz group endows the assay with high sensitivity. The amino acid sequence of the peptide has been chosen to ensure high specificity. The new assay requires no extraction, dialysis or other manipulation. The test is rapid and requires less than 100 μl serum.

DETAILED DESCRIPTION OF THE PREFERRED EMBODIMENT

Example 1: Synthesis

Melting points are uncorrected and were measured in open capillaries with the aid of Büchi Schmelzpunktbestimmungsapparat (Flawil, Switzerland). For thin layer chromatography, silica gel plates (DC-Karten SI F, Reidel de Haën A.G. West Germany) were used. These plates were developed with the following solvent systems: (I) chloroform-methanol (9:1, v/v); (II) chloroform-methanol (4:1, v/v); (III) methanol. Spots on the plates were located by ultraviolet light and by charring. Ninhydrin spray was used to detect compounds with unblocked terminal amino groups. Amino acid analysis was carried out after hydrolysis in 6 N hydrochloric acid for 20 hours in evacuated and sealed tubes at 110° C., using the Beckman model 120° C. amino acid analyzer. Anhydrous titrations with sodium methoxide in methanol-benzene 1:3 were performed.

Boc-Phe(NO$_2$)-Pro: A solution of Boc-Phe(NO$_2$)-ONSu (10 mmoles) in dioxane (30 ml) and a solution of proline (30 mmol) and sodium bicarbonate (60 mmol) in water (30 ml) were stirred overnight at room temperature, and the clear solution was concentrated in vacuo. The aqueous residue was acidified with a 1 M KHSO$_4$ solution and extracted three times with ethyl acetate. The combined organic extracts were washed with water, dried over Na$_2$SO$_4$ and evaporated in vacuo, yielding an oil which solidified under petroleum ether. Yield 3.2 g (78%); m.p. 100°–101° C.; R$_f$ in Solvent I=0.5; in Solvent II=0.75; and in Solvent III=0.6. Equivalent weight was found to be 407 (calc. 406) by titration with anhydrous sodium methoxide. The molar ratio of nitrophenylalanyl to prolyl was found to be 1.02 (calc. 1.00) by amino acid analysis. Analysis calculated for C$_{19}$H$_{25}$N$_3$O$_7$ (MW 407.43): N, 10.31. Found: N, 10.34.

Cbz-Abz-Gly: A solution of Cbz-ABz-OBSu (10 mmol) in dioxane (30 ml) and a solution of glycine (20 mmol) and sodium bicarbonate (40 mmol) in water (30 ml) were stirred overnight at room temperature. The clear solution was concentrated in vacuo. The aqueous residue was acidified with dilute HCl and the solid obtained was separated by filtration, yielding 3.1 g (95%); m.p. 110° C.; R$_f$ in Solvent II=0.5; in Solvent III=0.7. Equivalent weight was found to be 320 (calc. 328) by titration with anhydrous sodium methoxide. Analysis calculated for C$_{17}$H$_{16}$N$_2$O$_5$ (MW 328.33): C, 62.19; H, 4.91; N, 8.53. Found: C, 62.64; H, 5.24; N, 8.75.

Cbz-ABz-Gly-ONSu: To an ice-cold solution of Cbz-Abz-Gly (20 mmol) in ethylacetate-dioxane 1:3 (v/v, 100 ml), N-hydroxy-succinimide (20 mmol) and N,N'-dicyclohexylcarbodiimide (22 mmol) were added. After 20 hours at 4° C., a few drops of acetic acid were added and the N,N'-dicyclohexyl urea was filtered off. The solvent was removed in vacuo, and the solid residue was crystallized from isopropyl alcohol. Yield, 84%; m.p. 154°–155° C.; R$_f$ in chloroform-acetone 1:1 (v/v)=0.2. Analysis calculated for C$_{21}$H$_{19}$N$_3$O$_7$ (MW 425.39): C, 59.29; H, 4.50; N, 9.88. Found: C, 59.84; H, 4.78; N, 9.54.

Cbz-ABz-Gly-Phe(NO$_2$)-Pro: Boc-Phe(NO$_2$)-Pro (6 mmol) was dissolved in trifluoroacetic acid (5 ml). The solvent was removed in vacuo after 20 minutes and the oily residue was solidified upon treatment with ether. Yield, 95%. R$_f$ in Solvent III=0.4. Equivalent weight was found to be 213.7 (calc. 210.5) by titration with anhydrous sodium methoxide. This product was dissolved in water (40 ml) together with sodium bicarbonate (12 mmol) and the solution was mixed with a solution of Cbz-ABz-Gly-ONSu (6 mmol) in dioxane (40 ml). The mixture was stirred overnight at room temperature. The clear solution was concentrated in vacuo and the aqueous residue was acidified with dilute HCl. The solid obtained was filtered off, washed with water and dried in vacuo, yielding 2.8 g (76%), m.p. 84° C. R$_f$ in Solvent II=0.2; in Solvent III=0.7. Molar ratio of glycyl to nitrophenylalanyl to prolyl was found to be 1:1.04:1.06 (calc. 1.00:1.00:1.00). Analysis calculated for C$_{31}$H$_{31}$N$_5$O$_9$ (MW 617.62): C, 60,29; H, 5.06; N, 11.34. Found: C, 60.81; H, 4.81; N, 11.61.

ABz-Gly-Phe(NO$_2$)-Pro: This compound was prepared by removal of the benzyloxycarbonyl group from the peptide Cbz-Abz-Gly-Phe(NO$_2$)-Pro with HBr. Peptide concentration was 0.1 g/ml and the 30% HBr in acetic acid reagent contained anisol (10%). After 30 minutes, ether (100 ml) was added to precipitate a white solid, which was washed three times with ether, filtered off and dried in vacuo. R$_f$ in Solvent III=0.6, in chloroform-methanol 2:1 (v/v)=0.7. High voltage paper electrophoresis (28 V/cm, pH 3.5) revealed in minor fluorescent spot migrating ahead of the main dark non-fluorescent spot. An aliquot (400 mg) of the material, dissolved in 500 ml water containing 1% MeOH, was applied to a column of Poropak Q (1×3 cm). The small amount of fluorescent byproduct was washed out with ethanol-water (2:98), and the non-fluorescent peptide was eluted with ethanol (approx. 50 ml). The solvent was removed in vacuo and the solid residue was triturated with ether and filtered off, yielding 290 mg. This product migrated as a single spot in high voltage paper electrophoresis, m.p. 131° C. No Br$^-$ was detected in the material by halide titration. Anal. calc. for C$_{23}$H$_{25}$N$_5$O$_7$ (MW 483.47): C, 57.13; H, 5.21; N, 14.49. Found: C, 57.25; H, 5.39; N, 14.15.

EXAMPLE 2: Synthesis

Boc-Phe(NO$_2$)-NH$_2$: A solution of Boc-Phe(NO$_2$) (3.0 g) in N,N'-dimethylformamide (20 ml) was cooled to −10° C. N-methyl morpholine (1:1 ml) and isobutyl chloroformate (1.4 ml) were added. After 20 minutes a 25% aqueous solution of ammonia (2.0 ml) was added to the well mixed reaction mixture. After two hours during which the solution attained room temperature, water is added to precipitate the amide as a white solid. The water-washed product, dried in vacuo, yielded 2.9 g (97%). The material was shown to be homogeneous by thin layer chromatography. R$_f$ in Solvent II=0.8; R$_f$ in chloroform-acetone (4:1, v/v)=0.2.

Boc-Arg(NO$_2$)-Phe(NO$_2$)-NH$_2$: The unprotected p-nitrophenylalanine amide was prepared by dissolving Boc-Phe(NO$_2$)-NH$_2$ (2.7 g) in trifluoroacetic acid (10 ml), evaporation in vacuo after 30 minutes and washing the product repeatedly with ether. The Phe(NO$_2$)-NH$_2$.Tfa (2.4 g) and N-methylmorpholine (1.2 ml) were added to a solution of Boc-Arg(NO$_2$) (2.2 g), N-hydroxysuccinimide (700 mg) and N,N'-dicyclohexylcarbodiimide (1.6 g) in dioxane-ethylacetate-dimethylformamide (30:10:5) kept at 0° C. for 3 hours. Mixing was continued for 24 hours and the product was isolated and worked up the usual way, yielding 2.75 g (51.6%). The material was homogeneous as shown by thin layer chromatography. R$_f$ in chloroform-methanol (1:1, v/v)=0.8, R$_f$ in chloroform-methanol (2:1, v/v)=0.6.

Cbz-Abz-Gly-Arg(NO$_2$)-Phe(NO$_2$)-NH$_2$: A mixture of Cbz-ABz-Gly (2.0 g), N-hydroxysuccinimide (1.0 g) and N,N'=dicyloheyxlcarbodiimide (2.2 g) in chloroform (50 ml) was mixed in an ice bath for two hours, A solution of Arg (NO$_2$)-Phe(NO$_2$)-NH$_2$ trifluoroacetate (1.8 g) prepared by treatment of Boc-Arg(NO$_2$)-PHe(-NO$_2$)-NH$_2$ with trifluoroacetic acid as described under Boc-Arg(NO$_2$)-Phe(NO$_2$)-NH$_2$ and N-methyl morpholine (1.0 ml) in chloroform (40 ml) containing several drops of dimethylformamide were added and mixed at room temperature for 12 hours. The product was isolated and worked up the usual way yielding 2.8 g (58%). The solid material was chromatographically pure, R$_f$ in chloroform—methanol (3:1)=0.85, R$_f$ in chloroform—methanol (6:1)=0.60. Analysis calculated for C$_{32}$H$_{36}$N$_{10}$O$_{10}$ (MW 7207): N, 19.44. Found: N, 19.2.

ABz-Gly-Arg-Phe(NO$_2$)-NH$_2$ hydrofluoride: The protecting groups were removed from Cbz-ABz-Gly-Arg(NO$_2$)-NH$_2$ by treatment with hydrogen fluoride in presence of anisol at −10° C. for 90 minutes. The product was isolated and worked up by the usual ether precipitation, resulting in a solid material (yield 63%). R$_f$ in n-butanol-acetic acid-water (4:1:1, v/v)=0.6. Analysis calculated for $C_{24}H_{31}N_9O_6.7HF$ (MW 681.6): N, 18.49. Found 18.29.

EXAMPLE 3: Synthesis

Cbz-ABz-Eda: A mixture of ethylene diamine (45 ml) and dry dioxane (45 ml) was cooled to 0° C. Cbz-ABz-ONSu (4 g) dissolved in dioxane (30 ml) was added dropwise to the mixture and stirred for 3 hours at 0° C. The solid material was separated by filtration and the filtrate was evaporated to dryness. The residual oil was crystallized by adding of ice to yield 2.9 g (42%). $R_f$ in n-butanol-acetic acid-water (4:1:1)=0.5. Analysis calculated for $C_{17}H_{19}N_3O_3$ (MW 313): N, 13.4. Found: N, 13.1.

Boc-Pro-Eda-ABz(Cbz): A solution of Boc-Pro-ONSu (1 g) and N'N Dicyclohexylcarbodiimide (1.85 g) in chloroform (30 ml) was cooled to 0° C. After 1 hour, Cbz-ABz-Eda (2.55 g) was added and the mixture stored for 12 hours at room temperature. The N'N dicyclohexylurea was filtered off and the filtrate was treated as usual. Upon treatment with ethylacetato-petroleum ether, a white solid was obtained (2.9 g, 70%), $R_f$ in Solvent I=0.9. Analysis calculated for $C_{27}H_{34}N_4O_6$ (MW 510): N, 10.97. Found N, 11.1.

Boc-Pro-Pro-Eda-ABz(Cbz): This compound was synthesized analogously to the Boc-Pro-Eda-ABz(Cbz) from Boc-Pro-Pro (3.1 g) and Cbz-ABz-Eda (3.1 g). A viscous oil was obtained (4.0 g, 67% yield). Migrates as a single compound by thin layer chromatography on silica plates, $R_f$=0.3 in solvent I. Analysis calculated for $C_{32}H_4N_7)_7$ (MW 607); N, 11.53. Found: N, 11.1.

Boc-Phe(NO$_2$)-Pro-Eda-ABz(Cbz): Deprotection of Boc-Pro-Eda ABz(Cbz) (2.8 g) was achieved by treatment with trifluoroacetic acid (5 ml) for 30 minutes. The trifluoroacetate derivative was obtained by ether precipitation yielding 1.5 g (87%), $R_f$ in n butanol-acetic acid-water (4:1:1)=0.4. Boc-Phe(NO$_2$) (1.5 g) was dissolved in chloroform (30 ml) together with N-methyl morpholine (0.6 ml) and isobutyl chloroformate (0.7 ml) and cooled to −20° C. After 20 minutes this mixture was unified with the previously prepared trifluoroacetate derivative and N-methyl morpholine (0.6 ml). The mixture was stirred for 16 hours at room temperature. Then it was isolated by conventional techniques to yield upon final treatment with ethyl acetate-petroleum ether 3.0 g of a white solid (90%). $R_f$ in Solvent I=0.8, $R_f$ in chloroform-acetone (9:1)=0.5. Analysis calculated for $C_{36}H_{42}N_6O_9$ (MW 702.8): N, 11.96. Found: N, 11.5.

Boc-Phe(NO$_2$)-Pro-Pro-Eda-ABz(Cbz): This compound was synthesized analogously to Boc-Phe(NO$_2$)-Pro-Eda-Abz(Cbz). The reaction of Boc-Phe(NO$_2$) (1.1 g) with the trifluoroacetate salt of Pro-Pro-Eda-ABz(Cbz) (1.94 g) yielded a white solid (2.56 g) which was pure by thin layer chromatography on silica plates, $R_f$=0.8 in Solvent II. Analysis calculated for $C_{41}H_{49}N_7O_{10}$ (MW 799): N, 12.25. Found: N, 11.8.

Phe(NO$_2$)-Pro-Eda-ABz.2HBr: This material was prepared from Boc-Phe(NO$_2$)-Pro-Eda-ABz(Cbz) by the conventional treatment with HBr in acetic acid (30%) in presence of anisol (10%). The hydrobromide derivative was found to be homogeneous by high voltage paper electrophoresis in pyridine-acetic acid-water (pH 3.5). Equivalent weight of 310 was found from anhydrous titration with sodium methoxide. The calculated equivalent weight for $C_{23}H_{28}N_6O_5.2HBr$ (MW 630.37) is 315.

Phe(NO$_2$)-Pro-Pro-Eda-ABz.2HBr: This material was obtained from Boc-Phe(NO$_2$)-Pro-Pro-Eda-Abz(Cbz) by the conventional treatment with HBr in acetic acid (30%) in presence of anisol (10%). The hydrobromide peptide was homogeneous by high voltage paper electrophoresis in pyridine—acetic acid—water (pH 3.5). Equivalent weight of 354 was found by anhydrous titration with sodium methoxide. The equivalent weight calculated for $C_{28}H_{35}N_7O_6.2HBr$ is 363.5.

EXAMPLE 4: Synthesis

Boc-Phe(NO$_2$)-Pro-OBzl: Boc-Phe(NO$_2$)-OH (4.65 g, 15 mmol) was dissolved in chloroform (60 ml) and cooled to −20° C. N-methyl morpholine (1.7 ml) and isobutylchloroformate 2.1 ml were added and the reaction mixture was agitated for 20 minutes at −20° C. Proline benzyl ester hydrochloride (3.7 g, 15.3 mmol) and 1.8 ml of N-methyl morpholine were then added and the mixture stirred at room temperature overnight. The solution was washed with water, a 1 M solution of KHSO$_4$, with a dilute NaHCO$_3$ solution, and water. The organic phase was dried over anhydrous Na$_2$SO$_4$ and the solvent was removed by evaporation. Migrated as a simple component in thin layer chromatography on silica plates in chloroform—acetone (1:9) $R_f$=0.65, Nitrogen analysis found: 8.56% (expected: 8.45%).

Phe(NO$_2$)-Pro-OBzl.HCl: Boc-Phe(NO$_2$)-Pro-OBzl (8 mmol) was dissolved in dioxane (6.0 ml) and a 3.5 M HCl solution in dioxane (10 ml) was added. The material was precipitated after 15 hours with ether. The white solid was collected by filtration, washed with ether and dried in vacuo over NaOH and sulphuric acid. Yield: 3.28 g Migrated as a simple component on silica thin layer plates in butanolacetic n acid—water (4:1:1).

Example 5: Synthesis

Dns-Gly-Phe(NO$_2$)-pro-OBzl: Dansylglycine (2.0 g, 6.5 mmol), N-hydroxysuccinimide (0.75 g, 6.5 mmol) and DCCD (1.4 g, 6.79 mmol) were dissolved in a mixture of ethylacetate-dioxane (1:1, 100 ml) and cooled to 0°-4° C. The peptide HCl.Phe(NO$_2$)-Pro-OBzl (2.7 g, 7.6 mmol) was added after 40 minutes to the cold mixture, followed by dropwise addition of N-ethyl morpholine (2.5 ml). The mixture was stirred overnight at room temperature. The clear solution obtained after filtration was acidified with acetic acid, the solvent evaporated and the residue taken up in ethylacetate. The solution was washed with dilute HCl (pH about 4) containing sodium chloride and with a solution of sodium bicarbonate. The organic layer was dried over anhydrous sodium sulfate and the solvent was removed by evaporation. The residue was crystallized from isopropanol-isopropylether. Yield: 3.0 g, 48%.

Dns-Gly-Phe(NO$_2$)-Pro-OH: Dns-Gly-Phe(No$_2$)-Pro-OBzl (250 mg, 0.26 mmol) was dissolved in methanol (1.0 ml) and 1.3 M sodium hydroxide (3 ml) was added to the solution. After 40 minutes at room temperature, the methanol was removed by evaporation. The residue was diluted with water and extracted with ether, then acidified to pH 4.0 and extracted into ethylacetate. The solution was dried over anhydrous soldium sulfate, filtered and the solvent evaporated. The yellow residue was treated with petroleum ether until solidification of the product. Appears simple in thin layer chromatography on silica, migrating in MeOH-CHcl$_3$(1:1) with an $R_f$=0.45. The yield was 170 mg (73%).

EXAMPLE 6: Synthesis

Boc-Lys(Cbz-Abz)-Ala-NH.Bzl(NO₂)(I): Boc-Lys(Cbz-Abz). (cHxN)₂ (3 mmol) was converted into the free acid by acidifying in water with 1 M KHSO₄, extracting into ethyl acetate, drying over Na₂SO₄ and removal of the solvent by evaporation. The oily residue was dissolved in chloroform (40 ml) and the HBr salt of L-alanyl-p-nitrobenzylamine (3 mmol) was added to this solution together with N-ethylmorpholine (3 mmol). The solution was ice cooled, N,N'-dicyclohexycarbodiimide (3 mmol) was added and the mixture was stirred at 4° C. for 20 hours. The dicyclohexylurea formed was filtered off, the filtrate was washed with water and dried over Na₂SO₄. Removal of the solvent in vacuo yielded an oily product, which was purified by chromatography on a silica gel column using chloroform-acetone (9:1) as the eluant and ethylacetate-petroleumether precipitated. Yield (60%). Molar ratio of lysyl to alanyl was found to be 1.04 (calc. 1.00) by amino acid analysis. $C_{36}H_{44}N_6O_9$ (704.8): calc. N 11.9%; found 11.72%.

Boc-Lys(Cbz-Abz)-Phe-NHBzl(No₂) (II): This compound was prepared analogously to compound I, starting with 3 mmoles of Boc-Lys(Cbz.Abz): (cHxN) and 3 mmoles of the HBr salt of L-phenylalanyl-p-nitrobenzylamide. The yield was 75%. Molar ratio of lysyl to phenylalanyl was found to be 0.96 (calc. 1.00) by amino acid analysis. $C_{42}H_{48}N_6O_{18}$ (780.9): calc. N 10.7%; found N 10.57%.

Boc-Lys(Cbz-ABz)-Ala-Ala-NH-Bzl(NO₂) (III): This compound was prepared analogously to compound I, starting with 3 mmols of Boc-Lys(Cbz-ABz).(cHxN)₂ (3 mmol) and 3 mmols of the Hbr salt of L-alanyl-L-alanyl-p-nitrobenzylamide. The yield was 62%, molar ratio of alanyl to lysyl was found to be 2.04 (calc. 2.00) by amino acid analysis. $C_{39}H_{49}N_7O_{10}$ (775.9): calc. N 12.6%; found 12.4%.

Lys(ABz)-A-NH.Bzl(NO₂).2HBr[A=Ala(IV),-Phe(V) and Ala-Ala(VI)]:

These compounds were prepared from the corresponding compounds I-III by removal of protecting groups with HBr in acetic acid. The benzyloxycarbonyl and t-butyloxycarbonyl groups were simultaneously removed by treatment with 30% Hbr in acetic acid containing anisol (10%) for 15 minutes at room temperature. Yields were about 90%. The molar ratios of the constituent amino acid residues and electrophoretic migrations relative to lysine were for compounds IV: Ala/Lys=1.05 (calc. 1.00), $R_{Lys}$=0.55, for compound V: Phe/Lys=1.06 (calc. 1.00), $R_{Lys}$=0.46, for compound VI: Ala/Lys=1.98 (calc. 2.00); $R_{Lys}$=0.51. Incubation of each of the compounds IV, V and VI with leucine aminopeptidase (E.C. 3.4.11.1) produced quantitatively ε(2-aminobenzoyl)-L-lysisne, ($R_{Lys}$=0.26) and the other expected product as judged by high voltage paper electrophoresis using authentic markers.

The substrates produced according to the examples were used for determination of different enzymes according to the following:

The principle for the determination is based on the fact that the product formed by the enzymatic hydrolysis shows an emission which is much stronger from that of the substrate. Thus the substrate according to Example 1 ABz-Gly-Phe(NO₂)-Pro-OH has an absorption band with a maximal absorption at 284 nm, with the molar extinction coefficient 9860 $M^{-1}cm^{-1}$. When excited in this absorption band, (270-380 nm) a fluorescence is produced with a bell shaped emission spectrum (370-490 nm) having a maximum at 415 nm. The emission spectrum of the product of the enzymatic hydrolysis, namely ABz-Gly, has a similar emission spectrum but the intensity is 71 times higher.

Therefore, by means of measuring spectrofluoroimetrically the increase in fluorescence (emission at 410 nm, excitation at 360 nm or 376 nm) with time in presence of the enzyme one can readily follow the degree of the enzymatic hydrolysis which is proportional to the amount of 2-aminobenzoylglycine formed. The excess of substrate which is present does not interfere with the measurement if the absorption at the excitation or the emission wavelengths does not exceed the value of 0.1 when using a cell with a 1 cm path length or cells of other path lengths in which the absorption times path length is kept at the same value. The circumstances are very similar for the remaining substrates for the invention. The fluorimetric measurements were throughout made at an emission wavelength of 410 nm, with the emission slit set to 8 nm and at an excitation wavelength of 360 or 376 nm with the excitation slit set to 10 nm.

The fluorescence intensity of the product is increased in comparison to the intact substrate: 71 fold in the case of the hydrolysis of ABz-Gly-Phe(NO₂)-Pro (Example 1), 20 fold in the case of the hydrolysis of ABz-Gly-Arg-Phe(NO₂)-NH₂ (Example 2), 7.5 fold in the case of the hydrolysis of Phe(No₂)-Pro-Eda-ABz (Example 3), 3.4 fold in the case of Phe(NO₂)-Pro-Pro-Eda-ABz (Example 3), 5 fold in the case of Dns-Gly-Phe(No₂)-Pro-OH (Example 5), 27 fold in the case of Lys(ABz)-A-NHBzl(NO₂) for A=Ala or Phe and 18 fold or A=Ala-Ala (Example 6).

The quenching efficiency of the nitrophenyl and the dinitrophenyl group in their interaction with several fluorophores were determined by fluorescence measurements in which fluorescence of the chosen fluorescent compounds was measured in absence ($F_o$) and in presence (F) of the quencher at different concentrations of the quencher Q. The quenching efficiency $K_q$ was calculated from the well known Stern-Volmer equation $$F_o/F = 1 + K_q[Q]$$

As can be seen in Table I, 4-nitro-L-phenylalanine quenched with highest efficiency the fluorescent dansyl-L-alanine and 2-aminobenzoic acid. The least efficiently quenched fluorophores are the fluorescein derivatives. Using 2.4-dinitrophenyl-L-isoleucine as the quencher, the quenching efficiency increased markedly with dansyl-L-alanine and with fluorescein.

TABLE I

| Fluorophore | Quencher | λem nm | λexit nm | $K_q$ $M^{-1} \times 10^{-3}$ |
|---|---|---|---|---|
| Dansyl-L-alanine | Phe(NO₂) | 560 | 284 | 5.0 |
| Dansyl-L-alanine | Dnp-Ile | 560 | 360 | 15.0 |
| 2-amino benzoic acid | Phe(NO₂) | 410 | 284 | 5.0 |
| 1.8-amino naphthalene-sulfonic acid | Phe(NO₂) | 418 | 284 | 2.6 |
| anthracene | Phe(NO₂) | 412 | 284 | 2.2 |
| umbeliferone | Phe(NO₂) | 445 | 284 | 1.2 |
| eosin I | Phe(NO₂) | 540 | 284 | 0.15 |
| eosin Y | Phe(NO₂) | 540 | 284 | 0.15 |
| rhodamine B | Phe(NO₂) | 580 | 284 | 0.14 |
| fluoresceine | Phe(NO₂) | 515 | 284 | 0.13 |
| fluoresceine | Dnp-Ile | 515 | 360 | 1.63 |

Phe(NO₂): 4-nitro-L-phenylalanine; Dnp-Ile: 2.4-dinitro-L-isoleucine; λem: wavelength at which emission was measured; λexit: wavelength of excitation

Fluorimetric Assays

The rate of enzymic hydrolysis of the fluorogenic compound ABz-Gly-Phe(NO$_2$)-Pro by peptidyldipeptide hydrolases was monitored spectofluorometrically as follows. Samples of the partially purified bacterial (5-10 µl) or calf-lung peptidyldipeptide hydrolase (10-40 µl) were added to 3 ml of substrate solution (0.02-0.4 mM) in 0.05 tris-HCl, pH 8.0, containing 0.1 M NaCl, placed in an optical cell. No increase of fluorescence was obtained in the absence of enzyme. The increase in fluorescence (emission at 410 nm, excitation at 360 nm or 376 nm) with time in presence of the enzyme, was recorded continuously and the slope of the line was translated into molar concentrations of free ABz-Gly per minute using a calibration curve constructed by fluorescence measurements of solutions of authentic 2-aminobenzoylglycine under identical conditions. Dependence of the rate of hydrolysis on substrate concentration was established from initial rates, which were constant at least up to 10% hydrolysis. (Degree of hydrolysis, however, did not have to exceed 2% to obtain accurate measurements). Duplicates were highly reproducible, differing by not more than about 1% in the actual reading. The Km values obtained for the lung converting enzyme and the bacterial dipeptidyl carboxypeptidase were 0.21±0.10 mM and 0.16±0.10 mM respectively. They were calculated by the method of Lineweaver and Burk. Substrate concentrations were in range of 28-430 µM, and the experimental points did not deviate from the linear fit by more than 4%. Five points approximately equidistant on the 1/S ordinate were averages of two independent series of measurements.

The hydrolysis of ABz-Gly-Phe(NO$_2$)-Pro by human serum angiotensin I-converting enzyme was too slow for continuous measurement. Thus, the following procedure was applied. Human serum (5-40 µl) was added to a solution of the substrate (80.8 µM), in 0.05 M tris-HCl, pH 7.95, containing 1 M NaCl (final volume 0.5 ml). For studies of inhibition by [Asn$^1$, Val$^5$]angiotensin II, this mixture contained also the proper concentration of the inhibitor. After incubation for 30 minutes at 40° C., the reaction was stopped by adding EDTA (final concentration 8 mM) in the above buffer solution (2.5 ml). Identical solutions to which the EDTA solution was added prior to adding of the enzyme served as zero-time controls. The rate of hydrolysis was determined from the emission at 410 nm (upon excitation at 360 nm), corrected by substracting the emission of the zero-time control and expressed in terms of ABz-Gly concentrations per 30 minutes.

Fluorimetric Assay of Aminopeptidase-P: The rate of enzymatic hydrolysis of the fluorogenic compound Phe(NO$_2$)-Pro-Eda-Abz.2HBr was monitored spectrophotometrically as follows. Bacterial aminopeptidase-P (E.C. 3.4.11.9) (10 µl) was added to 0.5 ml of a solution of the substrate (10$^{-4}$-10$^{-3}$ M) in Veronal buffer (10 mM CoSo$_4$, 60 mM Na-Citrate, 50 mM Veronal pH 8.3). After incubation for 5 minutes at 40° C., the reaction was terminated by adding 1 M EDTA solution (10 µl) and the mixture was diluted with the above buffer to a final substrate concentration of 10$^{-4}$ M. As zero-time control served a similar mixture handled analogously except that the substrate solution contained 0.02 M EDTA. The rate of hydrolysis was determined from the emission at 410 nm (upon excitation at 360 nm), corrected by substracting the emission of the zero-time control and expressed in terms of ABz-Gly concentration per 5 minutes. From the dependence of the rate of hydrolysis on substrate concentration the Km value of 3×10$^{-3}$ M was calculated. In a similar manner aminopeptidase-P-like enzymes such as the aminoacylproline aminopeptidase in human serum and in calf-lung can be determined.

Fluorimetric assay of leucine aminopeptidase: The rate of enzymatic hydrolysis of the fluorogenic compounds Lys(ABz)-A-NH-Bzl(NO$_2$), A=Ala, Phe or Ala-Ala was followed spectrofluorimetrically as follows. A solution of leucine aminopeptidase (5 µl, 0.4 mg/ml in 0.05 M barbital, pH 8.6, 2 mM in MnCl$_2$, activated prior to the kinetic experiments by incubation at 37° C. for 2 hours) was added to 3 ml of 0.05 M tris-HCl, pH 7.8, containing the substrate (0.02-0.75 mM) and placed in an optical cell. The increase in fluorescence (emission at 410 nm, excitation at 310 nm) due to the liberation of Lys(ABz) was recorded continuously. In the absence of enzyme, no increase in fluorescence was observed. The increase in fluorescence intensities measured in presence of the enzyme was translated into concentrations of free Lys (ABz) using a calibration curve constructed by fluorescence measurements of solutions of authentic H-Lys(ABz)-OH under identical conditions.

Fluorimetric Assay of Trypsin: The rate of enzymatic hydrolysis of the fluorogenic compound ABz-Gly-Arg-Phe(NO$_2$)-NH$_2$ was monitored spectrofluorimetrically as follows. Samples of trypsin (E.C. 3.4.21.4) dissolved in 1 mM HCl (200 µg/ml) (10 µl) were added to 3.5 ml of the substrate solution (0.01 mM-0.1 mM) in 0.2 M Tris-HCl, pH 8.3 containing 50 mM CaCl$_2$, placed in an optical cell. No increase of fluorescence was obtained in the absence of enzyme. The increase in fluorescence (emission at 410 nm, excitation at 360 nm) with time in presence of the enzyme, was recorded continuously and the slope of the line was translated into molar concentration of ABz-Gly per minute using a calibration curve constructed by fluorescence measurements of autherntic ABz-Gly solutions. Dependence of the rate of hydrolysis on substrate concentration was established from initials rates. The Km value of 7.7×10$^{-5}$ M was calculated by the method of Lineweaver and Burk. Substrate concentrations were in the range of 10-100 µM.

| LIST OF ABBREVIATIONS | |
|---|---|
| ABz | o-aminobenzoyl |
| Arg | L-arginyl |
| Boc | t-butyloxycarbonyl |
| Cbz | benzyloxycarbonyl |
| Eda | —NH—CH$_2$—CH$_2$—NH— |
| EDTA | Ethylenediamine tetra acetic acid |
| Gly | glycyl- |
| Phe(NO$_2$) | p-nitro-L-phenylalanyl- |
| Pro | L-prolyl |
| Tfa | trifluoroacetate |
| Dns | 1-dimethylaminonaphtalene-5-sulfonyl ("dansyl") |
| DCCD | N,N'-dicyclohexylcarbodiimide |
| Cbz(NO$_2$) | p-nitrobenzyloxycarbonyl |
| NBZ1A | p-nitrobenzylamido |
| (cHxN)$_2$ | dicyclohexylamine |
| "umbeliferone" | 7-amido-4-methylcoumarine |
| Rhd | rhodaminyl |
| Enzymes: | Aminopeptidase-P or aminoacylproline aminopeptidase (E.C. 3.4.11.9) angiotensin-I-converting enzyme or peptidyldipeptide hydrolase (E.C. 3.4.15.1) |

LIST OF ABBREVIATIONS
-continued

Trypsin (E.C. 3.4.21.4)

We claim:

1. Substrate with high susceptibility to peptidyldipeptide hydrolases (E.C. 3.4.15), especially angiotensin-converting enzyme, which substrates are represented by the formula

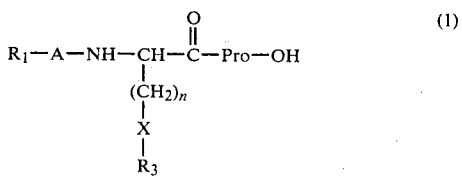

or salts thereof, where $R_1$ is selected from the group consisting of 1-diemthylaminonaphtalene-5-sulfonyl, 2-aminobenzoyl, 1.8-aminonaphtalenesulfonyl, anthracene-9-carbonyl, fluoresceinyl, tetrabromofluoresceinyl ("eosinyl"), and rhodaminyl; A is selected from the group consisting of glycyl, L-alanyl, L-leucyl, L-phenylalanyl and L-isoleucyl; n is 1-6; X is selected from the group consisting of a single bond, a carbonyl and imine (NH) group; $R_3$ is selected from the group consisting of nitrophenyl, dinitrophenyl, trinitrophenyl, nitrobenzyloxycarbonyl, dinitrobenzyloxycarbonyl, trinitrobenzyloxycarbonyl, nitrobenzoyl, dinitrobenzoyl, trinitrobenzoyl, ω-nitrophenylalkylamine having 1-4 carbon atoms in a straight chain, ω-dinitrophenylalkylamine having 1-4 carbon atoms in a straight chain and ω-trinitrophenylalkylamine having 1-4 carbon atoms in a straight chain.

2. Substrate according to claim 1 with high susceptibility to peptidyl-dipeptide hydrolases (E.C. 3.4.15), especially angiotensin-converting enzyme, which substrate is represented by the formula

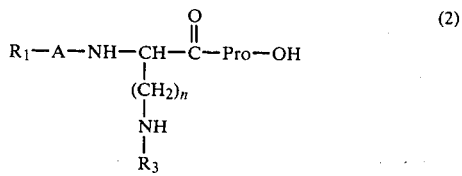

or salts thereof, where $R_1$ is selected from mono-, di-, or trinitrophenyl alkyl oxycarbonyl with 7-12 carbon atoms, a mono-, di-, or trinitrophenyl alkyl carbonyl with 7-12 carbon atoms; A may be selected from internal amino acid residues glycyl, L-alanyl, L-leucyl, L-phenylalanyl, L-isoleucyl; n is 3 or 4; $R_3$ is selected from the group consisting of 1-dimethylaminonaphtalene-5-sulfonyl, 2-aminobenzoyl, 1.8-aminonaphtalene-sulfonyl, anthracene-9-carbonyl, umbeliferone, fluoresceinyl, tetrabromofluoresceinyl ("eosinyl") and rhodaminyl.

3. The substrate of claim 1 which is ABz-Gly-Phe(-NO$_2$)-Pro-OH wherein ABz designates 2-amino benzoyl; Gly designates glycyl; Phe(NO$_2$) designates p-nitro-L-phenylalanyl and Pro designates L-prolyl.

4. The substrate of claim 1, which is Dns-Gly-Phe(-NO$_2$)-Pro-OH wherein Dns designates 1-dimethylaminonaphtalene-5-sulfonyl; Gly designates glycyl; Phe(NO$_2$) designates p-nitro-L-phenylalanyl and Pro designates L-prolyl.

5. The substrate of claim 1, which is Rhod-Gly-Phe(-NO$_2$)$_2$-Pro-OH wherein Rhod designates rhodaminyl; Gly designates glycyl; Phe(NO$_2$)$_2$ designates 2.4-dinitro-L-phenylalanyl and Pro designates L-prolyl.

6. The substrate of claim 2, which is NCbz-Gly-Lys-(ABz)-Pro-OH wherein NCbz designates 4-nitrobenzyloxycarbonyl; Gly designates glycyl; Lys(ABz) designates N$^\epsilon$-(2 aminobenzoyl)-L-lysyl and Pro is L-prolyl.

7. Substrate with high susceptibility to α-aminoacyl-peptide hydrolases (E.C. 3.4.11) which is represented by the formula

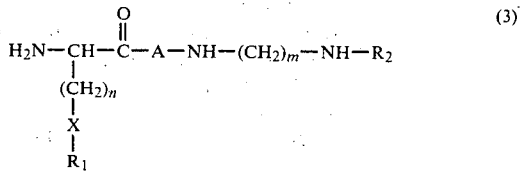

or the salts thereof; n is selected from 1, 2, 3 and 4; X is selected from a single bond, secondary amino group, carbonyl; $R_1$ is selected from nitrophenyl, dinitrophenyl, trinitrophenyl, nitrobenzyloxycarbonyl, dinitrobenzyloxycarbonyl, trinitrobenzyloxycarbonyl, nitrobenzoyl, dinitrobenzoyl, trinitrobenzoyl, ω-nitrophenylalkylamine having 1-4 carbon atoms in a straight chain, ω-dinitrophenylalkyl amine having 1-4 carbon atoms in a straight chain, ω-trinitrophenylalkyl amine having 1-4 carbon atoms in a straight chain; A is selected from the group consisting of one or two internal amino acid residues L-prolyl, glycyl, L-alanyl, L-leucyl, L-phenylalanyl, L-tyrosyl, L-lysyl, L-glutamyl, L-prolyl-L-prolyl and glutaminyl; m is selected from 1-6; $R_2$ is selected from the group consisting of 1-dimethylaminonaphtalene-5-sulfonyl, 2-aminobenzoyl, 1.8-dimethylaminonaphtalene-sulfonyl, anthracene-9-carbonyl, umbeliferone, fluoresceinyl, tetrabromofluoresceinyl ("eosinyl") and rhodaminyl.

8. Substrate with high susceptibility to α-aminoacyl peptide hydrolases (E.C. 3.4.11) which is represented by the formula:

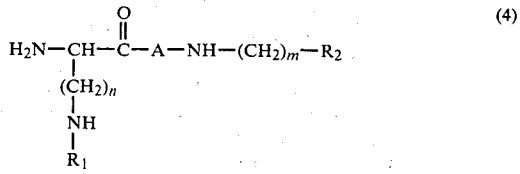

and salts thereof, where n is 3 or 4; $R_1$ is selected from 1-dimethylaminonaphtalene-5-sulfonyl, 2-aminobenzoyl, 1.8-aminonaphtalene-sulfonyl, anthracene-9-carbonyl, umbeliferone, fluoresceinyl, tetrabromofluoresceinyl ("eosinyl") and rhodaminyl; A is selected from L-alanyl, L-alanyl-L-alanyl, L-phenylalanyl, L-phenylalanyl-L-alanyl, L-alanyl-L-phenylalanyl, L-alanyl-L-leucinyl, L-leucinyl-L-alanyl, L-leucinyl, L-isoleucinyl, L-isoleucinyl-L-alanyl, L-alanyl-L-isoleucinyl, L-alanyl-L-lysyl and L-alanyl-l-glutamyl; m is an integer of 1 to 6; $R_2$ is selected from nitrophenyl, dinitrophenyl, trinitrophenyl, Cbz(NO$_2$)-NH and Cbz(NO$_2$)$_2$-NH where Cbz designates benzyloxycarbonyl.

9. The substrate of claim 8 which is N-(2-aminobenzoyl)-L-lysyl-L-alanyl-p-nitrobenzyl amide or the HCL, HBr or trifluoroacetyl salt thereof.

10. The substrate of claim 7, which is H-Phe(NO$_2$)-Pro-Eda-ABz, wherein Phe(NO$_2$) designates 4-nitro-L-phenylalanyl; Pro designates L-prolyl; Eda designates NH—CH$_2$—CH$_2$-NH, and ABz designates 2-aminobenzoyl.

11. The substrate of claim 7 which is H-Phe(NO$_2$)-Pro-Pro-Eda-ABz wherein Phe(NO$_2$) is 4-nitro-L-phenylalanyl; Pro is L-prolyl, Eda is NH—CH$_2$—CH$_2$—NH, and ABz is 2-aminobenzoyl.

12. The substrate of claim 8 which is H-Lys(ABz)-Ala-Phe(NO$_2$)-NH$_2$ wherein Lys(ABz) is N$^\epsilon$-(2-aminobenzoyl)-L-lysyl; Ala is L-alanyl; Phe(NO$_2$) is 4-nitro-L-phenylalanyl.

13. The substrate of claim 8 which is H-Lys(ABz)-Ala-Ala-Phe(NO$_2$)-NH$_2$ wherein Lys(ABz) is N$^\epsilon$-(2-aminobenzoyl)-L-lysyl; Ala is L-alanyl and Phe(NO$_2$) is 4-nitro-L-phenylalanyl.

14. Substrate with high susceptibility to peptide peptidohydrolases which is represented by the formula

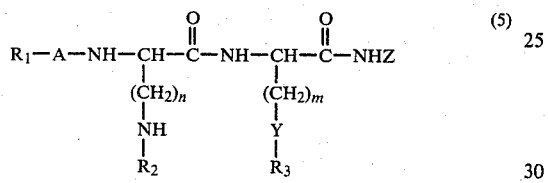
(5)

and its salts, where R$_1$ is selected from the group consisting of 1-dimethylaminonaphtalene-5-sulfonyl, 2-aminobenzoyl, 1.8-aminonaphtalenesulfonyl, anthracene-9-carbonyl, umbeliferone, fluoresceinyl, tetrabromofluoresceinyl ("eosinyl"), rhodaminyl; A is selected from glycyl, L-valyl, L-leucyl, L-prolyl and L-phenylalanyl-L-valyl; n is 3 or 4; R$_2$ is selected from hydrogen and guanyl; m is an integer of 1 to 4; Y is selected from a single bond, carbonyl, and an imine (NH) group; R$_3$ is selected from nitrophenyl, dinitrophenyl, trinitrophenyl, nitrobenzyloxycarbonyl, dinitrobenzyloxycarbonyl, trinitrobenzyloxycarbonyl, ω-nitrophenylalkyl having 1-4 carbon atoms in a straight chain, ω-trinitrophenylalkyl carbonyl having 1-4 carbon atoms in a straight chain, ω-nitrophenylalkylamino having 1-4 carbon atoms in a straight chain, ω-dinitrophenylalkylamino having 1-4 carbon atoms in a straight chain, and w-trinitroalkylamino having 1-4 carbon atoms in a straight chain; Z is selected from hydrogen, and acyl having from 1 to 6 carbon atoms, a C-terminal amino acid residue glycyl, L-alanyl, L-leucyl, L-phenylalanyl, L-prolyl, L-glutaminyl and their respective amides.

15. The substrate of claim 14 which is ABz-Gly-Arg-Phe(NO$_2$)-NH$_2$ wherein ABz is 2-aminobenzoyl; Gly is glycyl; Arg is L-arginyl, Phe(NO$_2$) is 4-nitro-L-phenylalanyl.

16. The substrate of claim 14 which is ABz-Gly-Lys-Phe(NO$_2$)-NH$_2$ wherein ABz is 2-aminobenzoyl; Gly is glycyl; Phe(NO$_2$) is 4-nitro-L-phenylalanyl.

17. The substrate of claim 14 which is ABz-Val-Arg-Phe(NO$_2$)-NH$_2$ wherein ABz is 2-aminobenzoyl, Val is L-valyl, Arg is L-arginyl, Phe(NO$_2$) is 4-nitro-L-phenylalanyl.

18. Intramolecularly quenched fluorogenic substrate with high susceptibility to peptide peptidohydrolases which is represented by the formula

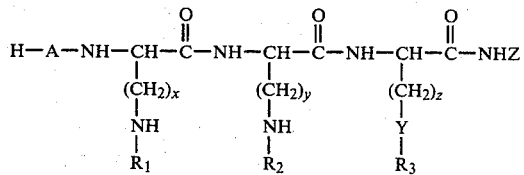

or salts thereof, where A is selected from glycyl, D-valyl, D-phenylalanyl and L-phenylalanyl; x is 2, 3 or 4; R$_1$ is selected from the group consisting of 1-dimethylaminonaphtalene-5-sulfonyl, 2-aminobenzoyl, 1.8-aminonaphthalenesulfonyl, anthracene-9-carbonyl, fluoresceinyl, tetrabromofluoresceinyl ("eosinyl"), rhodaminyl; y is 3 or 4; R$_2$ is hydrogen or guanyl; z is an integer of 1 to 4; Y is selected from a single bond, carbonyl and imine (NH); R$_3$ is selected from the group consisting of nitrophenyl, dinitrophenyl, trinitrophenyl, nitrobenzyloxycarbonyl, dinitrobenzyloxycarbonyl, trinitrobenzyloxycarbonyl, ω-nitrophenylalkyl having 1-4 carbon atoms in a straight chain, ω-trinitrophenylalkyl carbonyl having 1-4 carbon atoms in a straight chain, ω-nitrophenylalkylamino having 1-4 carbon atoms in a straight chain, ω-dinitrophenylalkylamino having 1-4 carbon atoms in a straight chain, and ω-trinitrophenylalkylamino, having 1-4 carbon atoms in a straight chain.

19. The substrate of claim 18 which is D-Val-Lys(ABz)-Arg-Phe(NO$_2$)-NH$_2$ wherein D-Val is D-valyl; Lys(ABz) is N$^\epsilon$-(2-aminobenzyol)-L-lysyl; Arg is L-arginyl; Phe(NO$_2$) is 4-nitro-L-phenylalanyl.

* * * * *